(12) United States Patent
Chen et al.

(10) Patent No.: US 6,576,769 B2
(45) Date of Patent: Jun. 10, 2003

(54) PROCESS TO PREPARE (2S)-2-(DIPROPYLAMINO)-6-ETHOXY-2,3-DIHYDRO-1H-INDENE-5-CARBOXAMIDE

(75) Inventors: Jiong Jack Chen, Kalamazoo, MI (US); Arthur Glenn Romero, Kalamazoo, MI (US); Styrbjorn Bystrom, Taby (SE)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/163,836

(22) Filed: Jun. 6, 2002

(65) Prior Publication Data

US 2002/0151750 A1 Oct. 17, 2002

Related U.S. Application Data

(62) Division of application No. 09/952,413, filed on Sep. 14, 2001.
(60) Provisional application No. 60/233,542, filed on Sep. 18, 2000.

(51) Int. Cl.[7] .............................................. C07D 209/48
(52) U.S. Cl. ........................ 548/473; 564/163; 564/164; 564/165

(58) Field of Search ......................................... 548/473

(56) References Cited

U.S. PATENT DOCUMENTS

| 4,232,014 A | | 11/1980 | Mathison et al. ............ 424/324 |
| 5,728,869 A | | 3/1998 | Briner ........................ 562/452 |
| 6,084,130 A | | 7/2000 | Romero et al. .............. 564/163 |
| 6,103,752 A | * | 8/2000 | Glen et al. .................. 514/414 |
| 6,429,212 B1 | * | 8/2002 | Hashimoto .................. 514/309 |

* cited by examiner

*Primary Examiner*—Shailendra Kumar
(74) *Attorney, Agent, or Firm*—Bruce Stein; John H. Engelmann

(57) ABSTRACT

The present invention is a process, including intermediates, to produce (2S)-2-dipropylamino)-6-ethoxy-2,3-dihydro-1H-indene-5-carboxamide

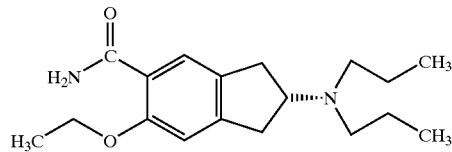

which is a useful pharmaceutical agent.

8 Claims, No Drawings

US 6,576,769 B2

PROCESS TO PREPARE (2S)-2-(DIPROPYLAMINO)-6-ETHOXY-2,3-DIHYDRO-1H-INDENE-5-CARBOXAMIDE

CROSS-REFERENCE TO RELATED APPLICATIONS

This patent application is a divisional application of U.S. patent application Ser. No. 09/952,413, filed Sep. 14, 2001, which claims the benefit of U.S. Provisional Patent Application No. 60/233,542, filed Sep. 18, 2000, under 35 USC 119(e)(i). The entire disclosure of which is herein incorporated by reference.

BACKGROUND OF THE INVENTION

1. Field of the Invention

The present invention is a process, including intermediates, to produce (2S)-2-dipropylamino-6-ethoxy-2,3-dihydro-1H-indene-5-carboxamide which is a useful pharmaceutical agent.

2. Description of the Related Art

U.S. Pat. No. 6,084,130 discloses racemic (2S)-2-(dipropylamino)-6-ethoxy-2,3-dihydro-1H-indene-5-carboxamide, see Example 38, and a process to prepare it.

U.S. provisional application Serial No. 60/184,020 discloses optically pure (2S)-2-(dipropylamino)-6-ethoxy-2,3-dihydro-1H-indene-5-carboxamide as well as a method of its preparation.

SUMMARY OF INVENTION

Disclosed is N-[(2S)-6-Ethoxy-2,3-dihydro-1-oxo-1H-inden-2-yl]-2,2,2-trifluoroacetamide.

Also disclosed is N-[(1S,2S)-6-Ethoxy-2,3-dihydro-1-hydroxy-1H-inden-2-yl]-2,2,2-trifluoroacetamide.

Further disclosed is N-[(2S)-5-Ethoxy-2,3-dihydro-1H-inden-2-yl]-2,2,2-trifluoroacetamide.

Additionally disclosed are compounds selected from the group consisting of:
2-[(1S,2S)-6-ethoxy-2,3-dihydro-1-hydroxy-1H-inden-2-yl]-1H-isoindole-1,3(2H)-dione,
2-[(1R,2S)-6-ethoxy-2,3-dihydro-1-hydroxy-1H-inden-2-yl]-1H-isoindole-1,3(2H)-dione,
N-[(1S,2S)-6-ethoxy-2,3-dihydro-1-hydroxy-1H-inden-2-yl]-2-(hydroxymethyl)benzamide and
N-[(1R,2S)-6-ethoxy-2,3-dihydro-1-hydroxy-1H-inden-2-yl]-2-(hydroxymethyl)benzamide.

Disclosed is a process for the preparation of N-[(2S)-6-Ethoxy-2,3-dihydro-1-oxo-1H-inden-2-yl]-2,2,2-trifluoroacetamide (V) which comprises:

(1) contacting O-ethyl-L-tyrosine (IV) with an activating reagent,
(2) contacting the reaction mixture of step (1) with a Lewis acid for a period of less than 24 hr,
(3) quenching the reaction mixture of step (2) with a protic solvent.

Also disclosed is a process for the preparation of 2-[(2S)-6-ethoxy-2,3-dihydro-1-oxo-1H-inden-2-yl]-1H-isoindole-1,3(2H)-dione (XV) which comprises:

(1) contacting (αS)-α-[(4-ethoxyphenyl)methyl]-1,3-dihydro-1,3-dioxo-2H-isoindole-2-acetic acid (XIV) with an activating reagent,
(2) contacting the reaction mixture of step (1) with a Lewis acid for a period of less than 24 hr,
(3) quenching the reaction mixture of step (2) with a protic solvent.

DETAILED DESCRIPTION OF THE INVENTION

U.S. Pat. 6,084,130, EXAMPLE 38, discloses (2S)-2-dipropylamino)-6-ethoxy-2,3-dihydro-1H-indene-5-carboxamide in racemic form and a process for its preparation. U.S. provisional application Serial No. 60/184,020 discloses optically pure (2S)-2-(dipropylamino)-6-ethoxy-2,3-dihydro-1H-indene-5-carboxamide as well as a method of its preparation. The present patent application discloses a process to produce optically pure (2S)-2-dipropylamino)-6-ethoxy-2,3-dihydro-1H-indene-5-carboxamide.

Optically pure (2S)-2-dipropylamino)-6-ethoxy-2,3-dihydro-1H-indene-5-carboxamide is made by the process of the present invention as set forth in the CHARTS and EXAMPLES 1–18.

The processes of Steps (D) and (O), the transformation of the amine (IV) to the trifluoroacetamide (V) are inventive. What is described for the process of Step (D) is the same as for the process of Step (O), only the reactant is different resulting in a correspondingly different product.

In the process of Step (D), the O-ethyl-L-tyrosine (IV) is reacted with an activating reagent. It is preferred that the activating reagent be selected from the group consisting of trifluoroacetic anhydride, thionyl chloride and oxalyl chloride. It is more preferred that the activating reagent is trifluoroacetic anhydride. The O-ethyl-L-tyrosine (IV) is contacted with the activating agent in an inert solvent, preferably a chlorinated hydrocarbon solvent, more preferably methylene chloride. The reaction is operable from about −20° to about 80°, preferably from about 0° to about 40°. The reaction mixture of step (1) is then contacted with a Lewis acid. It is preferred that the Lewis acid be ferric chloride or gallium chloride, more preferably ferric chloride. The reaction of step (2) is preferably performed in an inert solvent, more preferably a chlorinated hydrocarbon solvent, even more preferably methylene chloride and is operable from about −20° to about 80°, preferably from about 0° to about 40°. The reaction mixture of step (2) is then quenched with a suitable quenching agent as is known to those skilled in the art. It is preferred that the quenching of step (3) be performed in an inert solvent, preferably a chlorinated hydrocarbon solvent, more preferably methylene chloride and is operable from about −20° to about 80°, preferably from about 0° to about 40°. The process of Step (O) is virtually the same except it starts with (αS)-α-[(4-ethoxyphenyl)methyl]-1,3-dihydro-1,3-dioxo-2H-isoindole-2-acetic acid (XIV).

In the conversion of amino compound (VI) to the dipropylamino compound (VII) it is apparent to those skilled in the art that other similar alkylating reagents can be utilized in place of n-bromopropane, such as n-propyliodide, etc. Also, other bases can be utilized in place of the phosphate base, such as sodium carbonate, organic tertiary amine bases such as diisopropylethylamine, etc. The preferred procedure is to use n-bromopropane and tribasic sodium phosphate. Additionally, it is apparent to those skilled in the art that reductive amination procedures can also be used to perform this chemical transformation, including using propanal in the presence of a hydride transfer reducing reagent such as sodium triacetoxyborohydride, sodium cyanoborohydride, etc. Alternatively, the amine can be repetitively acylated to form the propionamide of the amine and then reduced to the amine with lithium aluminum hydride, diisobutylhydride, a borane reagent, etc. two times to introduce the required propyl groups. The preferred method to obtain (VIII) is to heat (VII) with n-bromopropane in the presence of tribasic sodium phosphate. An analytical sample can be crystallized from ethyl acetate/hexane.

In the conversion of the dipropyl compound (IX) to the bromo compound (X), it will be apparent to one skilled in the art that other methods of brominating (IX) exist, such as direct treatment with bromine, N-bromosuccinimide, dibromohydantoin, etc. Other acid catalysts can also be utilized, such as acetic acid and other low molecular weight carboxylic acids, mineral acids, organic sulfonic acids, etc. Trifluoroacetic acid is the preferred acid catalyst.

In the transformation of the bromo compound (X) to the amide (XI), it is readily apparent to one skilled in the art that a variety of palladium catalysts ($PdCl_2$, $Pd_n(dba)_m$, etc.) and associated ligands (triphenylphosphine, tri-ortho-tolulyphosphine, etc) can be utilized in varying catalytic quantities.

The ALTERNATE PROCESS chart, discloses an alternate process for the transformation of O-ethyl-L-tyrosine (IV) to the dipropylamino compound (VII). See also EXAMPLEs 14–16

(2S)-2-dipropylamino)-6-ethoxy-2,3-dihydro-1H-indene-5-carboxamide (XI) is known to be a useful pharmaceutical agent, see U.S. Pat. No. 6,084,130.

DEFINITIONS AND CONVENTIONS

The definitions and explanations below are for the terms as used throughout this entire document including both the specification and the claims.

Definitions

All temperatures are in degrees Celsius.

TLC refers to thin-layer chromatography.

HPLC refers to high pressure liquid chromatography.

DMF refers to dimethylformamide.

Chromatography (column and flash chromatography) refers to purification/separation of compounds expressed as (support, eluent). It is understood that the appropriate fractions are pooled and concentrated to give the desired compound(s).

LC-MS refers mass spectroscopy analysis after liquid-liquid chromatography separation.

rt refers to retention time.

CMR refers to C-13 magnetic resonance spectroscopy, chemical shifts are reported in ppm ($\delta$) downfield from TMS.

NMR refers to nuclear (proton) magnetic resonance spectroscopy, chemical shifts are reported in ppm (d) downfield from TMS.

FMR refers to F-19 magnetic resonance spectroscopy, chemical shifts are reported in ppm ($\delta$) downfield from TMS.

TMS refers to trimethylsilyl.

$[\alpha]_D^{25}$ refers to the angle of rotation of plane polarized light (specific optical rotation) at 25° with the sodium D line (589A).

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

HRMS refers to high resolution mass spectrometry.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

N-t-butoxycarbonyl-L-tyrosine (II)

L-Tyrosine (I, 9.06 g, 50 mmol) is suspended in dioxane/water (1/1, 180 ml). Triethylamine (10.45 ml, 75 mmol) is added. The reaction mixture is cooled to −10° and di-tert-butyl dicarbonate (12.0 g, 55 mmol) is added. After 1 hr at −10°, the reaction is warmed to 20–25°e. The suspension is stirred at 20–25° for 18 hr. The resulting mixture is concentrated and then partitioned in ethyl acetate (90 ml) and water (45 ml). The aqueous phase is collected and adjusted to pH 1 using hydrochloric acid (1 M). The aqueous mixture is extracted with ethyl acetate (180 ml). The extract is dried over magnesium sulfate, filtered and concentrated to give the title compound, NMR (DMSO-$d_6$) $\delta$9.15, 7.01, 6.95, 6.64, 3.98, 2.86, 2.68 and 1.32; CMR (DMSO-$d_6$) $\delta$174.1, 156.2, 155.8, 130.3, 128.3, 115.3, 78.4, 55.8, 36.0 and 28.5; MS (CI, $NH_3$) m/z (relative intensity) 299, 282, 243, 226, 182 and 124.

Example 2

N-tert-Butoxycarbonyl-O-ethyl-L-tyrosine (III)

N-t-butoxycarbonyl-L-tyrosine (II, EXAMPLE 1, (235 g, 835 mmol) is dissolved in sodium hydroxide (4N, 705 mL)

at 20–25°. Diethyl sulfate (210 mL, 1.60 mol) is added over 15–20 min. The reaction mixture is stirred for 2 hr, then it is cooled with ice-bath (internal temperature around 15°). Ethyl acetate (1400 mL) is added, followed by slow addition of hydrochloric acid (3N, 1410 mL) for 1 hr. The ethyl acetate layer is separated, and the aqueous layer is extracted with ethyl acetate (1400 mL). The ethyl acetate phase is concentrated to about 200 mL, then hexane (1600 mL) is added. The mixture is stirred in an ice-bath for 2 hr, filtered, washed with hexane (800 mL) in 3 portions. The precipitate is dried to give the title compound. The filtrate is concentrated, suspended in ethyl acetate/hexane (80/450 mL) for 2 hr, filtered and washed with hexane (250 mL) in 3 portions and dried to give additional title compound, NMR (MeOH-$d_4$) $\delta$7.11, 6.80, 4.22, 4.05, 3.08, 2.86 and 1.36; CMR $\delta$175.4, 159.3, 157.8, 131.3, 130.4, 115.4, 80.5, 64.4, 56.4, 37.9, 28.7 and 15.2.

Example 3

O-Ethyl-L-tyrosine (IV)

N-tert-Butoxycarbonyl-O-ethyl-L-tyrosine (III, EXAMPLE 2, 195 g, 632 mmol) is suspended in THF (1200 mL), p-toluenesulfonic acid monohydrate (240 g, 1.26 mol) is added at 20–25°. The resulting mixture is heated at reflux for 2 hr. The mixture is neutralized with sodium hydroxide (2N, about 700 mL) to pH between 5 and 6 at 20–25°. The resulting mixture is stirred at 5° for 2 hr before it is filtered. The cake is washed with THF/water (4/1, 50 mL×3). The precipitate is dried to give the title compound. The filtrate is removed of all volatile, adjusted pH again to give more precipitate. The precipitate is dried to give additional title compound, NMR ($D_2O$/NaOH) $\delta$7.14, 6.88, 4.02, 3.40, 2.88, 2.73 and 1.30; CMR ($D_2O$/NaOH) $\delta$182.8, 157.0, 131.4, 131.0, 64.8, 57.8, 40.3 and 14.3.

Example 4

N-[(2S)-6-Ethoxy-2,3-dihydro-1-oxo-1H-inden-2-yl]-2,2,2-trifluoroacetamide (V)

O-Ethyl-L-tyrosine (IV, EXAMPLE 3, 10.5 g, 50 mmol) is suspended in methylene chloride (84 mL). Trifluoroacetic anhydride (21 mL, 150 mmol) is added over 20 min at 20–25 deg. The resulting mixture is added dropwise to a solution of ferric chloride (8.92 g, 55 mmol) in methylene chloride (80 mL) over 1 hr. After the reaction is completed, it is quenched with water (150 mL). The organic layer is separated and swapped into methanol (50 mL). The mixture is cooled to −20° for 1 hr and then filtered and dried to give the title compound, NMR (DMSO-d6) $\delta$9.89, 7.43, 7.27, 7.10, 4.04, 3.42, 2.94 and 1.30; CMR (DMSO-$d_6$) $\delta$201.4, 158.7, 156.6, 144.4, 136.9, 128.0, 124.8 and 116.2; HRMS for $C_{13}H_{12}F_3NO_3$ [M+1]=288.0847, found=288.0844.

Example 4a

N-[(2S)-6-Ethoxy-2,3-dihydro-1-oxo-1H-inden-2-yl]-2,2,2-trifluoroacetamide (V)

O-Ethyl-N-trifluoroacetyl-L-tyrosine (XIII, Example 17, 1.52 g, 5 mmol) and ferric chloride (0.89 g, 5 mmol) are suspended in methylene chloride (36 mL). Trifluoroacetic anhydride (2.12 mL, 15 mmol) is added over 1 hr at 20–25°. The reaction is stirred for 1 hr and then quenched with water (36 mL). The organic layer is separated and mixed with methanol (7 mL). The mixture is cooled to −20° for 1 hr and then filtered to give the same title compound as EXAMPLE 4.

Example 5

N-[(1S,2S)-6-Ethoxy-2,3-dihydro-1-hydroxy-1H-inden-2-yl]-2,2,2-trifluoroacetamide (VI)

N-[(2S)-6-Ethoxy-2,3-dihydro-1-oxo-1H-inden-2-yl]-2,2,2-trifluoroacetamide (V, EXAMPLE 4, 718 mg, 2.5 mmol) is suspended in ethanol (25 ml) and cooled to −10°. Sodium borohydride (113 mg, 3 mmol, 1.2 equiv.) is added and the reaction mixture stirred for 1 hr. The reaction is quenched with hydrochloric acid (1 M; 15 ml) followed by water (15 ml). The resulting suspension is stirred at 5° for 1 hr. The title compound is collected by vacuum filtration, washed with water and dried in a vacuum oven to give the title compound, TLC $R_f$=0.9 (ammonium hydroxide/methanol/methylene chloride; 1.5/13.5/85); NMR (MeOH) $\delta$7.10, 6.89, 6.80, 5.08, 4.39, 4.01, 3.20, 2.72 and 1.36; CMR $\delta$160.1, 159.2, 145.1, 131.5, 126.5, 117.4, 116.5, 110.5, 80.0, 64.6, 61.6, 35.1 and 15.2; FMR (DMSO-$d_6$) $\delta$-74.6. MS (CI, $NH_3$) m/z (relative intensity) 307 (100), 291 (30), 272 (90), 176 (50).

Example 6

(1S,2S)-2-Amino-6-ethoxy-2,3-dihydro-1H-inden-1-ol (VII)

N-[(1S,2S)-6-Ethoxy-2,3-dihydro-1-hydroxy-1H-inden-2-yl]-2,2,2-trifluoroacetamide (VI, EXAMPLE 5, 723 mg, 2.5 mmol) and potassium carbonate (1.73, 12.5 mmol, 5 equiv.) is suspended in methanol (25 ml) and water (6.25). The reaction mixture is heated at reflux for 1 hr. The mixture is concentrated and the residue partitioned in hydrochloric acid (1 M; 10 ml), water (10 ml) and methyl t-butyl ether (25 ml). The mixture is heated until the solids dissolved. The aqueous phase is collected and washed with hot methyl t-butyl ether (25 ml). The combined methyl t-butyl ether extracts are concentrated to dryness to give the title compound, TLC $R_f$=0.5 (ammonium hydroxide/methanol/methylene chloride; 1.5/13.5/85); NMR (MeOH) $\delta$7.08, 6.87, 6.75, 4.68, 4.01, 3.35, 3.08, 2.51 and 1.36; CMR $\delta$159.8, 146.1, 132.7, 126.3, 116.0, 110.7, 83.6, 64.6, 63.7, 37.9 and 15.2; MS (CI, $NH_3$) m/z (relative intensity) 206, 194 (100), 176, 161.

Example 7

(1S-trans)-2-(Dipropylamnino)-6-ethoxy-2,3-dihydro-1H-inden-1-ol (VIII)

(1S,2S)-2-Amino-6-ethoxy-2,3-dihydro-1H-inden-1-ol (VII, EXAMPLE 6) is added to acetonitrile with excess tribasic sodium phosphate and n-bromopropane and stirred until analysis indicates that starting material is completely converted to the dipropyl-substituted material (VII). The preferred procedure is to heat the slurry at 60–70° for two–three days. The reaction is cooled, filtered, and the solids rinsed with methyl t-butyl ether. The mixture is concentrated under reduced pressure and then more methyl t-butyl ether is added and the mixture extracted with aqueous sodium hydroxide. The organic layer is washed with excess dilute aqueous hydrochloric acid and the aqueous hydrochloric acid extracts are combined and back-washed with methyl t-butyl ether and then made basic with concentrated aqueous sodium hydroxide. This aqueous mixture is then washed with methyl t-butyl ether. The ether is removed under reduced pressure to obtain the same title compound (VIII) as EXAMPLE 8, mp 74–75°.

Example 8

(1S-trans)-2-(Dipropylamino)-6-ethoxy-2,3-dihydro-1H-inden-1-ol (VIII)

N-[(2S)-6-Ethoxy-2,3-dihydro-1-oxo-1H-inden-2-yl]-2,2,2-trifluoroacetamide (V, EXAMPLE 4, 4.13 g, 15 mmol) is suspended in ethanol (45 ml) and cooled to −15°. Sodium borohydride (2.83 g, 75 mmol, 5 equiv.) is added and the reaction mixture gradually warmed to 20–25° overnight. The reaction mixture is concentrated to dryness and then suspended in acetonitrile (105 ml). Sodium phosphate tribasic (8.12 g, 49.5 mmol, 3.3 equivalents) is added and the mixture heated to 40°. n-Propylbromide (12.26 ml, 135 mmol, 9 equivalents) is added and reaction is heated to 65°. Heating is continued for 48 hr. The reaction mixture is filtered and the filtrate concentrated. The concentrate is partitioned in methyl t-butyl ether (100 ml) and sodium hydroxide (1 M, 50 ml). The organic layer is collected and acidified with hydrochloric acid (3 M, 50 ml). The aqueous phase is collected and the pH is adjusted to 13 using sodium hydroxide (50%, 25 ml). The product is extracted into methyl t-butyl ether (100 ml) and concentrated to give the title compound, TLC $R_f$=0.9 (ammonium hydroxide/methanol/methylene chloride, 1.5/13.5/85); NMR δ7.04, 6.90, 6.79, 5.04, 4.01, 3.39, 2.87, 2.72, 2.59–2.48, 1.54–1.48, 1.39 and 0.90; CMR δ158.4, 144.2, 131.5, 125.6, 115.4, 109.2, 77.3, 73.2, 63.6, 53.6, 29.9, 21.1, 14.8, 11.9; MS (CI, $NH_3$) m/z (relative intensity) 278 (100), 248 (70), 236 (20).

Example 9

(S)-5-ethoxy-2,3-dihydro-N,N-dipropyl-1H-inden-2-amine (IX)

(1S)-Trans-2-(dipropylamino)-6-ethoxy-2,3-dihydro-1H-inden-1-ol (VIII, EXAMPLE 8, 85 kg) is placed into a hydrogenation reactor with a catalytic amount of Palladium on carbon (5%) and acetic acid (2185 kg) is added as solvent. Acetic anhydride (63 kg, 2 equiv.) is added and the mixture is hydrogenated at 40 p.s.i. while heating to 60–65° C. When analysis indicated that the starting material (VIII) had been completely converted into product (IX) the mixture is cooled and filtered. The solvent is removed by heating under reduced pressure and the residue is extracted with methyl t-butyl ether and aqueous sodium hydroxide (added until the solution indicated a pH greater than 12). The aqueous layer is back extracted with more methyl t-butyl ether and the combined organic layers are washed with dilute aqueous sodium hydroxide solution. The methyl t-butyl ether solution is then extracted twice with aqueous hydrochloric acid (1 N), adding sufficient acid to wash all of the amine product into the aqueous layer). The aqueous acid layers are combined and washed with methyl t-butyl ether after which the aqueous layer is adjusted to a pH greater than 12 and then extracted with two portions of dichloromethane. The dichloromethane is washed with water and the solvent removed by heating under reduced pressure to give the same title compound (IX) as EXAMPLE 11. An analytical sample can be prepared as the p-toluenesulfonic acid salt from methanol/diethylether to give the title compound, mp=136–138°; $[\alpha]^{25}D$=11° (c=0.82, methanol).

Example 10

N-[(2S)-5-Ethoxy-2,3-dihydro-1H-inden-2-yl]-2,2,2-trifluoroacetamide (XII)

N-[(2S)-6-Ethoxy-2,3-dihydro-1-oxo-1H-inden-2-yl]-2,2,2-trifluoroacetamide (V, EXAMPLE 4, 5.75 g, 20 mmol) is dissolved in 28.8 ml of trifluoroacetic acid and triethylsilane (9.6 ml, 60 mmol, 3 equiv.) is added. The reaction mixture is heated at reflux for 3 hr and then concentrated under reduced pressure. The product is partitioned between saturated sodium carbonate (30 ml) and ethyl acetate (60 ml). The organic layer is collected and concentrated to a solid. The solid is purified by flash chromatography eluting with ethyl acetate/hexane (3/7) to give the title compound; TLC $R_f$=0.64 (ethyl acetate/hexane; 30/70); NMR δ7.12, 6.75, 6.48, 4.76, 4.01, 3.32, 2.81 and 1.40; CMR δ58.7, 156.8, 141.2, 131.4, 125.4, 116.4, 113.8, 110.9, 63.6, 51.6, 39.9, 38.8 and 14.8; FMR (DMSO-$d_6$) δ74.5. MS (CI, $NH_3$) m/z (relative intensity) 291 (100), 273 (10), 243 (20), 160 (30), 132 (20). HRMS (FAB) calculated for $C_{13}H_{12}F_3NO_2$ [M+1]=272.0898, found=272.0896.

Example 11

(2S)-5-Ethoxy-2,3-dihydro-N,N-dipropyl-1H-inden-2-amine (IX)

N-[(2S)-5-Ethoxy-2,3-dihydro-1H-inden-2-yl]-2,2,2-trifluoroacetamide (XII, EXAMPLE 10, 1.36 g, 5 mmol) is suspended in 15 ml of ethanol. Sodium borohydride (567 mg, 15 mmol, 3 equiv.) is added and the mixture stirred at 20–25° for 18 hr. The reaction mixture is concentrated to dryness and suspended in acetonitrile (35 ml). Sodium phosphate tribasic (2.71 g, 16.5 mmol, 3.3 equiv.) and propyl bromide (4.10 ml, 45 mmol, 9 equiv.) is added and the reaction mixture heated at 65° for 24 hr. The reaction mixture is filtered and the filtrate concentrated to dryness. The residue is partitioned in sodium hydroxide (1 M) and methyl t-butyl ether. The organic phase is collected and concentrated. The concentrate is chromatographed to give the title compound, TLC $R_f$=0.91 (ammonium hydroxide/methanol/methylene chloride; 1.5/13.5/85); NMR δ7.02, 6.73, 6.65, 3.97, 3.60, 2.97–2.92, 2.90–2.78, 2.48, 1.48, 1.39 and 0.92; CMR δ157.9, 143.3, 133.8, 125.0, 112.7, 110.5, 63.6, 63.5, 53.4, 36.9, 35.8, 20.3, 14.8 and 11.9; MS (EI) m/z (relative intensity) 261 (10), 232 (40), 204 (30), 177 (30), 160 (70), 132 (100).

Example 12

(R)-5-bromo-6-ethoxy-2,3-dihydro-N,N-dipropyl-1H-inden-2-amine hydrochloride (X)

Pyridinium perbromide (64 kg, 1.34 equiv.) is added to dichloromethane solvent and cooled to −20°. A −20° solution of (S)-5-ethoxy-2,3-dihydro-N,N-dipropyl-1H-inden-2-amine (IX, EXAMPLE 9, 39 kg) and trifluoroacetic acid (50 kg, 3.0 equiv) dissolved in dichloromethane is added. After stirring for several hours the reaction is warmed to 0°. When analysis indicated that all of the starting material (IX) had been consumed, the reaction is quenched with a reducing agent such as aqueous sodium bisulfate. Aqueous sodium hydroxide is then added to make the pH greater than 12 and most of the dichloromethane and pyridine are removed by heating under reduced pressure. The residue is extracted several times with methyl t-butyl ether, the organic layers are combined, stirred with magnesium sulfate, filtered, and the solvent removed by heating under reduced pressure to give the title compound in crude form. An analytical sample is crystallized from methanol/methyl t-butyl ether as the hydrochloride salt to give the title compound as the hydrochloride salt in purified form, mp=202–204°.

The free base of the title compound has the following characteristics, NMR (300 MHz, CDCl$_3$) δ0.86, 1.41–1.55, 2.43–2.49, 2.76–2.99, 3.57, 4.05, 6.73, 7.31; $[\alpha]^{25}$D=5° (c=1.01, methanol).

Example 13

(2S)-2-dipropylamino)-6-ethoxy-2,3-dihydro-1H-indene-5-carboxamide (XI)

(R)-5-bromo-6-ethoxy-2,3-dihydro-N,N-dipropyl-1H-inden-2-amine (X, as its hydrochloride salt, EXAMPLE 12, 48 kg) is dissolved in dimethylformamide with a catalytic amount of palladium acetate (0.5 kg, 0.019 equiv.) and 1,3-bis(diphenylphosphino)propane (1.85 kg, 0.038 equiv.), potassium carbonate (39 kg, 2.42 equiv.), and hexamethyldisilylazane (90 kg, 4.77 equiv.). The reaction is heated 100° C. being preferred) under an atmosphere of carbon monoxide until analysis indicated that all of the bromo starting material (X) had been consumed. The reaction is cooled, diluted with methyl t-butyl ether (MTBE) and water, and filtered to remove solids. The two-phase mixture is made basic and product is extracted into MTBE. The extracts are washed with dilute base, then water. The mixture is placed under reduced pressure and heated to remove volatile reagents and solvents. The residue is slurried with aqueous hydrochloric acid and filtered. The filtrate is extracted with MTBE. The aqueous phase is made basic with aqueous sodium hydroxide, and the product is extracted into MTBE. The extracts are washed again with water and then dried by distillation. The resulting MTBE solution is treated with magnesium silicate adsorbent, which is removed by filtration. The MTBE filtrate is concentrated and heptane added at approximately 50° followed by gradual cooling to induce the crystallization of the product which is filtered and dried. mp=100–101°; NMR (CDCl$_3$) δ7.99, 7.87, 6.78, 6.12, 4.17–4.11, 3.72–3.61, 3.06–2.78, 2.48–2.43, 1.54–1.41 and 0.87; $[\alpha]^{25}$D=+4.94° (c=0.842, MeOH).

Example 14

(αS)-α-[(4-Ethoxyphenyl)methyl]-1,3-dihydro-1,3-dioxo-2H-isoindole-2-acetic acid (XIV)

O-Ethyl-L-tyrosine (IV, EXAMPLE 3, 20.9 g, 100 mmol) and N-carbethoxyphthalimide (23.0 g, 105 mmol) are suspended in water (210 mL). Sodium carbonate (11.1 g, 105 mmol) is added and the mixture is stirred at 20–25° for 24 hr. Hydrochloric acid (1N, 200 mL) is added to the resulting mixture and stirred for 2 hr. The mixture is filtered, washed with water (100 mL) and dried to give the title compound, NMR (MeOH-d$_4$) δ7.78–7.72, 7.14, 6.68, 5.11, 3.90, 3.47 and 1.28; CMR (MeOH-d$_4$) δ172.2, 169.0, 159.2, 135.6, 132.8, 130.9, 130.3, 124.2, 115.5, 64.3, 54.8, 34.7 and 15.0.

Example 15

2-[(2S)-6-Ethoxy-2,3-dihydro-1-oxo-1H-inden-2-yl]-1H-isoindole-1,3(2H)-dione (XV)

(αS)-α-[(4-Ethoxyphenyl)methyl]-1,3-dihydro-1,3-dioxo-2H-isoindole-2-acetic acid (XIV, EXAMPLE 14, 13.6 g, 40 mmol) is suspended in methylene chloride (40 mL). Trifluoroacetic anhydride (11.4 mL, 80 mmol) is added over 20 min at 20–25°. The resulting mixture is added dropwise to a solution of ferric chloride (6.81 g, 42 mmol) in methylene chloride (80 mL) over 1 hr. After the reaction is complete, it is quenched with water (80 mL). The organic layer is separated and concentrated. The residue is purified with a by column chromatography (silica gel; ethyl acetate/hexane, 20/80) to give the title compound, NMR δ7.85, 7.73, 7.38, 7.26, 5.10, 4.07, 3.52, 3.30 and 1.43; CMR δ200.0, 167.4, 159.0, 143.5, 135.9, 134.1, 132.0, 127.3, 125.3, 123.5, 106.2, 63.9, 54.2, 31.2 and 14.6; HRMS (FAB) calculated for $C_{19}H_{15}NO_4$ $[M+1]$=322.1079, found=322.1085.

Example 16

2-[(1S,2S)-6-ethoxy-2,3-dihydro-1-hydroxy-1H-inden-2-yl]-1H-isoindole-1,3(2H)-dione and 2-[(1R,2S)-6-ethoxy-2,3-dihydro-1-hydroxy-1H-inden-2-yl]-1H-isoindole-1,3(2H)-dione (XVI) and N-[(1S,2S)-6-ethoxy-2,3-dihydro-1-hydroxy-1H-inden-2-yl]-2-(hydroxymethyl)benzamide and N-[(1R,2S)-6-ethoxy-2,3-dihydro-1-hydroxy-1H-inden-2-yl]-2-(hydroxymethyl)benzamide (XVII)

2-[(2S)-6-Ethoxy-2,3-dihydro-1-oxo-1H-inden-2-yl]-1H-isoindole-1,3(2H)-dione (XV, EXAMPLE 15, 276 mg, 0.86 mmol) and sodium borohydride (98 mg, 2.6 mmol) are suspended in 2-propanol (7.7 mL) and water (1.3 mL). After 24 hr, LC-MS indicated formation of the title compounds (XVI) and (XVII) with a mass spectrum of 323 and 327 respectively. Additional sodium borohydride (38 mg, 1 mmol) is added and the mixture is stirred for an additional hr. The suspension is taken up in water/methylene chloride. Aqueous citric acid solution is added. The organic layer is separated and concentrated to give the title compound (XVII).

Example 17

O-Ethyl-N-(trifluoroacetyl)-L-tyrosine (XIII)

O-Ethyl-L-tyrosine (IV, EXAMPLE 3, 20.9 g, 100 mmol) is suspended in methanol (100 mL), tetramethylguanidine (TMG) (12.5 mL, 100 mmol) is added, followed by ethyl trifluoroacetate (14 mL, 120 mmol). The mixture is stirred at 20–25 deg for 48 hr and the resulting mixture is concentrated to remove most of the methanol and excess ethyl trifluoroacetate. The residue is dissolved in water (40 mL), added hydrochloric acid (100 mL of 1.0 M) to adjust the pH<3. The mixture is stirred at 20–25° for at least 2 hr, then filtered. The precipitate is suspended in water (50 mL), stirred for 0.5 hr, then filtered. This wash process is repeated once. Then the precipitate is dried in oven at 55° for 48 hr to give the title compound, NMR (DMSO-$d_6$) δ12.9, 9.72, 7.15, 6.82, 4.46, 3.98, 3.15, 2.92 and 1.31; CMR (DMSO-$d_6$) δ171.8, 157.6, 157.7, 130.3, 129.0, 116.1, 63.2, 54.6, 35.1 and 15.0; FMR (DMSO-d6) δ-74.7; HRMS (FAB) calculated for $C_{13}H_{14}F_3NO_4$ [M+1]=306.0953, found=306.0952.

Example 18

(1S,2S)-2-Amino-6-ethoxy-2,3-dihydro-1H-inden-1-ol (VII)

N-[(1S,2S)-6-ethoxy-2,3-dihydro-1-hydroxy-1H-inden-2-yl]-2-(hydroxymethyl)benzamide and N-[(1R,2S)-6-ethoxy-2,3-dihydro-1-hydroxy-1H-inden-2-yl]-2-(hydroxymethyl)benzamide (XVII, Example 16, 200 mg, 0.61 mmol) is dissolved in acetic acid (2.5 mL). The reaction mixture is stirred for 18 hr at 80°. Then the mixture is partitioned between methylene chloride and water. The aqueous phase is separated and adjusted to pH=10 using aqueous ammonium. The product is extracted with methylene chloride. The organic layers are concentrated to give the same title compound (VII) as EXAMPLE 6 and its cis-diastereomer.

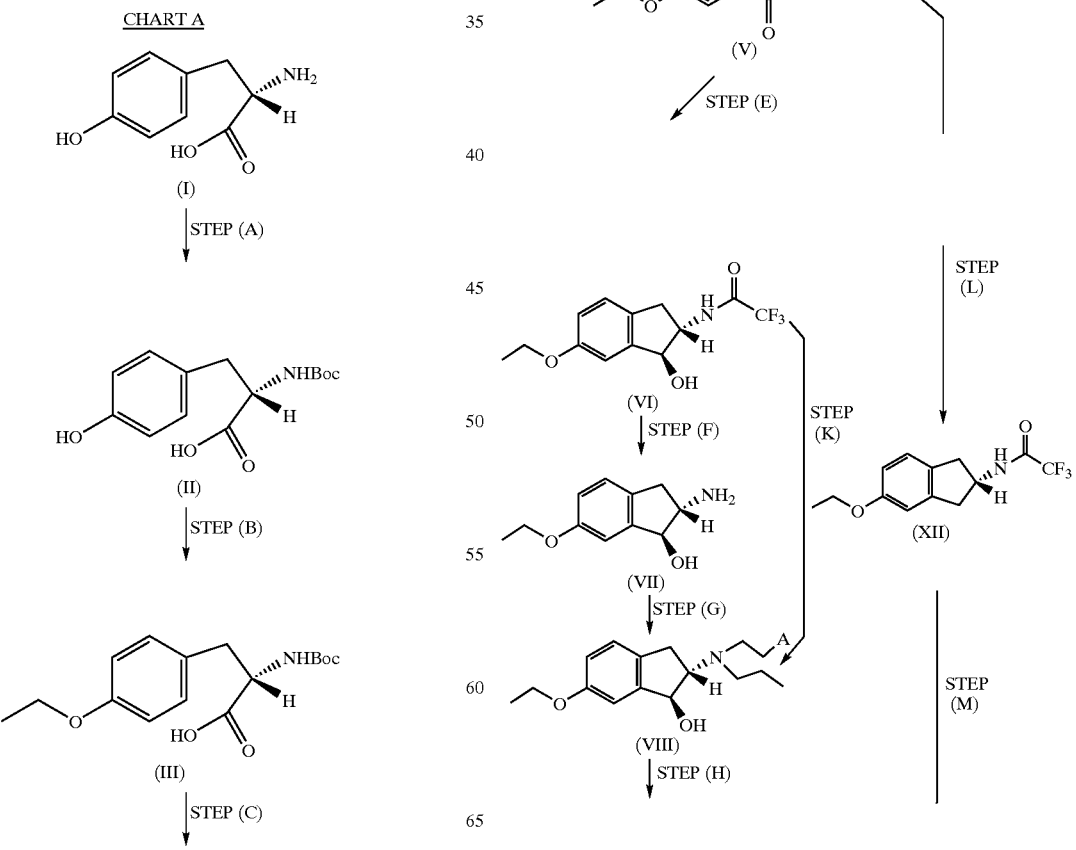

-continued
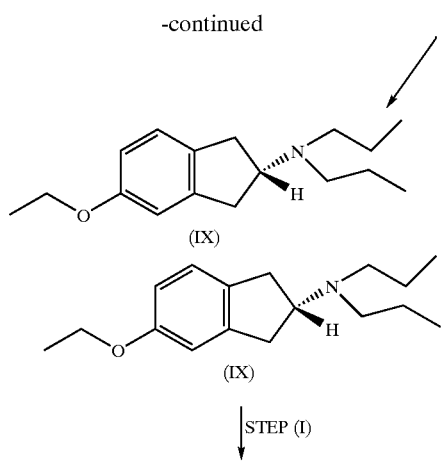
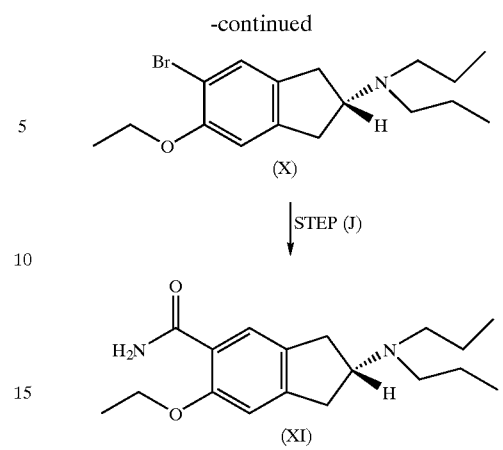
ALTERNATE PROCESS
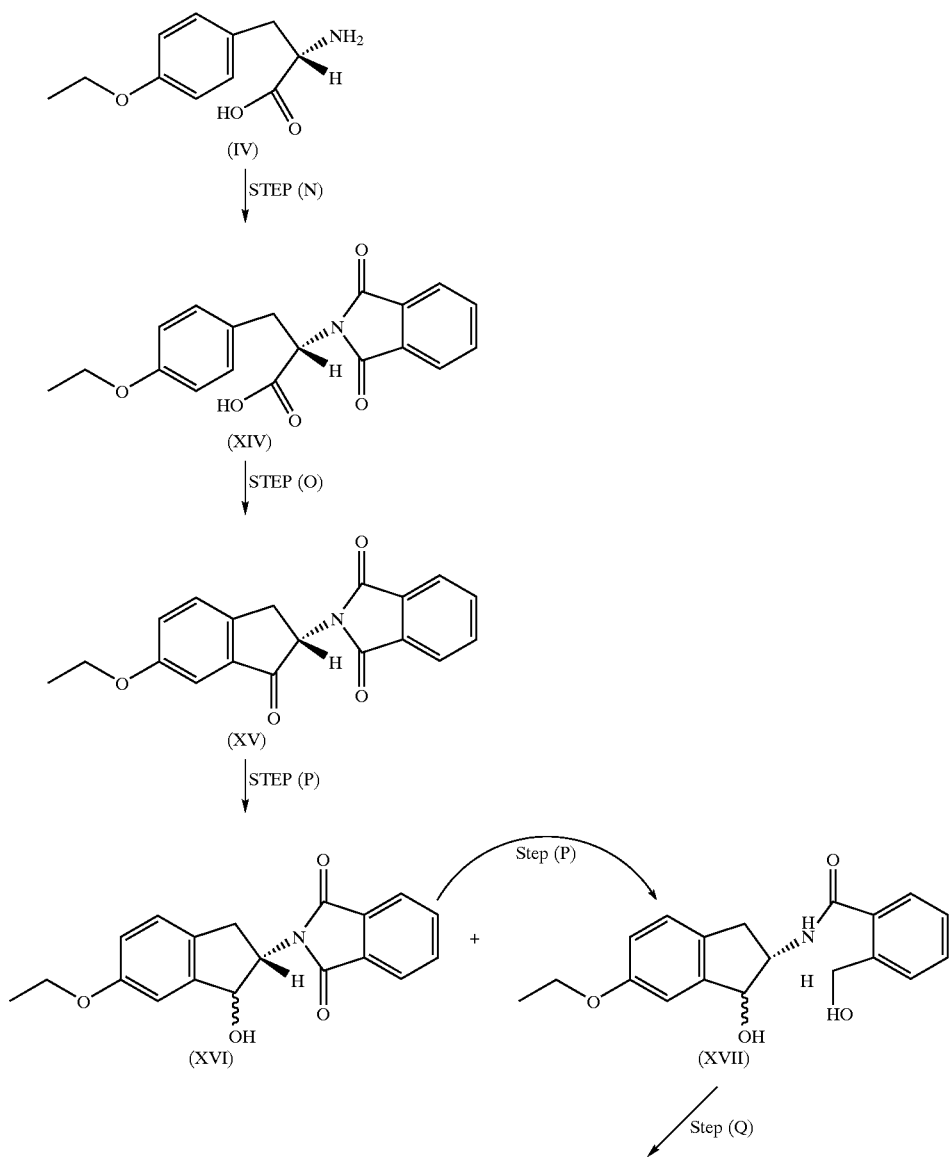

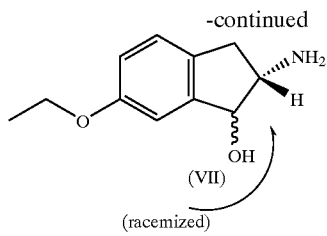

(VII)
(racemized)

What is claimed is:

1. A compound selected from the group consisting of:
   2-[(1S,2S)-6-ethoxy-2,3-dihydro-1-hydroxy-1H-inden-2-yl]-1H-isoindole-1,3(2H)-dione, and
   2-[(1R,2S)-6-ethoxy-2,3-dihydro-1-hydroxy-1H-inden-2-yl]-1H-isoindole-1,3(2H)-dione.

2. A process for the preparation of 2-[(2S)-6-ethoxy-2,3-dihydro-1-oxo-1H-inden-2-yl]-1H-isoindole-1,3(2H)-dione (XV) which comprises:
   (1) contacting (αS)-α-[(4-ethoxyphenyl)methyl]-1,3-dihydro-1,3-dioxo-2H-isoindole-2-acetic acid (XIV) with an activating reagent,
   (2) contacting the reaction mixture of step (1) with a Lewis acid for a period of less than 24 hr,
   (3) quenching the reaction mixture of step (2) with a protic solvent.

3. A process according to claim 2 where the activating reagent is selected from the group consisting of trifluoroacetic anhydride, thionyl chloride and oxalyl chloride.

4. A process according to claim 3 where the activating reagent is trifluoroacetic anhydride.

5. A process according to claim 2 where the Lewis acid is ferric chloride or gallium chloride.

6. A process according to claim 5 where the Lewis acid is ferric chloride.

7. A process according to claim 2 where the quenching agent is selected from the group consisting of water, aqueous acids and aqueous alcohols.

8. A process according to claim 7 where the quenching agent is water.

* * * * *